United States Patent [19]
Allen et al.

[11] Patent Number: 6,149,637
[45] Date of Patent: Nov. 21, 2000

[54] ELASTOMERIC DISPOSABLE ABSORBENT ARTICLE AND METHOD OF MAKING SAME

[75] Inventors: Patrick Jay Allen; Tracey Elaine Beckman; John Michael Blevins, all of Cincinnati; Louis John Viltro, Hamilton; William Robert Vinnage, Cincinnati, all of Ohio

[73] Assignee: The Procter & Gamble Company, Cincinnati, Ohio

[21] Appl. No.: 08/176,056

[22] Filed: Jan. 3, 1994

[51] Int. Cl.[7] ........................................................ A61F 13/15
[52] U.S. Cl. ................ 604/366; 604/385.22; 604/385.23; 604/385.29; 604/396
[58] Field of Search ........................................ 604/365, 366, 604/385.1, 385.2, 386, 388, 389, 390, 391, 392–396; 2/70, 71, 72, 75, 80

[56] References Cited

U.S. PATENT DOCUMENTS

| | | |
|---|---|---|
| 1,329,119 | 1/1920 | George . |
| 1,595,051 | 8/1926 | George . |
| 1,695,109 | 12/1928 | Kosloff . |
| 2,252,992 | 8/1941 | Steiner . |
| 2,397,838 | 4/1946 | Chavannes . |
| 2,429,177 | 10/1947 | Young . |
| 2,434,111 | 1/1948 | Hawley, Jr. et al. . |
| 2,521,020 | 9/1950 | Prescott .......................................... 2/71 |
| 2,522,421 | 9/1950 | Wolf ................................................ 2/71 |
| 2,523,079 | 9/1950 | Walter et al. . |
| 2,555,434 | 6/1951 | Anderson . |
| 2,564,369 | 8/1951 | Miller ............................................ 2/71 |
| 2,594,229 | 4/1952 | Snyder et al. . |
| 2,597,877 | 5/1952 | Le Clair . |
| 2,839,088 | 6/1958 | Biever ..................................... 604/396 |
| 2,897,108 | 7/1959 | Harwood ................................. 604/366 |
| 3,237,625 | 3/1966 | Johnson . |
| 3,599,640 | 8/1971 | Larson . |
| 3,842,837 | 10/1974 | Sward . |
| 3,916,491 | 11/1975 | Kampf . |
| 4,105,484 | 8/1978 | Newton et al. . |
| 4,205,679 | 6/1980 | Repke et al. . |
| 4,355,425 | 10/1982 | Jones et al. . |
| 4,364,787 | 12/1982 | Radzins . |
| 4,496,360 | 1/1985 | Joffe et al. . |
| 4,610,680 | 9/1986 | LaFleur . |
| 4,610,681 | 9/1986 | Strohbeen et al. . |
| 4,619,649 | 10/1986 | Roberts . |
| 4,641,381 | 2/1987 | Heran et al. . |
| 4,646,362 | 3/1987 | Heran et al. . |
| 4,662,874 | 5/1987 | Korpman . |
| 4,671,793 | 6/1987 | Hults et al. . |
| 4,731,066 | 3/1988 | Korpman ................................. 604/586 |
| 4,747,846 | 5/1988 | Boland et al. ........................ 604/385.1 |
| 4,789,699 | 12/1988 | Kieffer et al. . |
| 4,862,546 | 9/1989 | Kwack . |
| 4,895,809 | 1/1990 | Wilson et al. ........................ 604/385.1 |
| 4,925,520 | 5/1990 | Beaudoin et al. . |
| 4,936,840 | 6/1990 | Proxmire .............................. 604/385.2 |

(List continued on next page.)

FOREIGN PATENT DOCUMENTS

| | | |
|---|---|---|
| 0 477 802 A1 | 4/1992 | European Pat. Off. . |
| 0 526 868 A2 | 2/1993 | European Pat. Off. . |
| 1222034 | 3/1959 | France . |
| 91-335616/46 | 1/1990 | Japan . |
| 364845/1992 | 12/1992 | Japan . |
| 2 244 909 | 12/1991 | United Kingdom . |
| WO 90/04374 | 5/1990 | WIPO . |
| WO 90/04375 | 5/1990 | WIPO . |

*Primary Examiner*—John G. Weiss
*Assistant Examiner*—K. M. Reichle
*Attorney, Agent, or Firm*—Steven W. Miller; David M. Weirich; Jacobus C. Rasser

[57] ABSTRACT

A disposable absorbent article, such as a baby diaper, a child's training pant, an adult incontinent garment, or the like, having an elasticized chassis which provides laterally oriented contractive forces about the lower torso of the wearer. In a particularly preferred embodiment, the absorbent article will resemble a skirt or, alternatively, a pair of "boxer shorts".

4 Claims, 9 Drawing Sheets

U.S. PATENT DOCUMENTS

| | | |
|---|---|---|
| 4,938,753 | 7/1990 | Van Gompel et al. . |
| 4,938,757 | 7/1990 | Van Gompel et al. . |
| 4,940,464 | 7/1990 | Van Gompel et al. . |
| 4,943,340 | 7/1990 | Ujimoto et al. . |
| 5,032,120 | 7/1991 | Freeland et al. . |
| 5,043,036 | 8/1991 | Swenson . |
| 5,087,253 | 2/1992 | Cooper . |
| 5,087,255 | 2/1992 | Sims . |
| 5,106,382 | 4/1992 | Henry . |
| 5,151,051 | 9/1992 | Buell . |
| 5,169,706 | 12/1992 | Collier, IV et al. . |
| 5,171,239 | 12/1992 | Igaue et al. . |
| 5,185,011 | 2/1993 | Strasser . |
| 5,188,627 | 2/1993 | Igaue et al. . |
| 5,236,430 | 8/1993 | Bridges . |
| 5,246,433 | 9/1993 | Hasse et al. . |

ELASTOMERIC DISPOSABLE ABSORBENT ARTICLE AND METHOD OF MAKING SAME

FIELD OF THE INVENTION

The present invention relates to disposable absorbent article such as baby diapers, children's training pants, adult incontinence garments, and the like. The present invention relates more particularly to disposable training pants, which are placed in position on the wearer by inserting the wearer's legs into the leg openings and sliding the disposable absorbent article into position about the wearer's lower torso.

BACKGROUND OF THE INVENTION

Infants, children, and other incontinent individuals wear disposable absorbent articles to receive and contain urine and other bodily exudates. It is very desirable that the absorbent article fit snugly about the lower torso of the wearer to reduce the risk of urine, feces, or other bodily fluids leaking from the absorbent article and soiling the wearer's clothing, bed sheets, etc. It has been found that the fit of an absorbent article can be greatly improved by making the article elastically contractible.

Prior training pants have been elasticized using elastic elements disposed in the training pants such that the waist opening and leg openings are at least partially encircled with elasticized bands. This method of using elastic elements is shown in U.S. Pat. Nos. 4,610,680 to LaFleur; 4,610,681 to Strohbeen, et al.; 4,641,381 to Heran, et al.; 4,909,804 to Douglas, Sr.; and 4,960,414 to Meyer.

Another method of elasticizing disposable training pants is shown in U.S. Pat. Nos. 4,490,464; 4,938,753; and 4,938,757 all of which issued to Van Gompel, et al. These patents disclose a pant-like garment formed by attaching discrete stretchable members to the side edges of the main body of the garment.

Another method of elasticizing disposable training pants is shown in U.S. Pat. No. 5,246,433 which issued on Sep. 21, 1993 to Margaret H. Hasse, Russell P. Bridges, and Steven W. Miller. This patent discloses a unitary disposable garment having laminate earflaps which are ring-rolled or otherwise mechanically stretched to form elasticized earflap portions which are unitary with the disposable garment.

However, it has been found that a training pant having a fully elasticized chassis will fit the wearer's lower torso more snugly and will reduce the risk of urine, feces, or other bodily fluids leaking from the garment. It is therefore an object of the present invention to provide a disposable garment, such as disposable training pants, having a fully elasticized chassis which provides a more garment-like appearance and fits more snugly about the lower torso of the wearer.

It is also an object of the present invention to provide a method of manufacturing a disposable garment, such as disposable training pants, having a fully elasticized chassis which provides a more garment-like appearance and fits more snugly about the lower torso of the wearer.

It is also an object of the present invention to provide an absorbent article having a fully elasticized chassis and having fixed sides, which is very garment-like in appearance and feel so a toilet training child will distinguish it from a diaper and will easily adjust to cloth undergarments.

SUMMARY OF THE INVENTION

According to the present invention, a method of making a disposable garment, such as training pants, incontinent garments and the like, having a fully elasticized chassis comprising an elastomeric laminate is provided.

The method comprises the steps of laterally stretching an elastomeric, pressure-sensitive adhesive film, securing a gatherable lamina to one side of the film; securing a gatherable lamina to the other side of the film to form an elastomeric laminate; cutting leg cut-outs from the elastomeric laminate to form a chassis having a front portion, a rear portion, and a crotch portion; folding the chassis in about the crotch region; joining the edges of the front portion to the edges of the rear portion to form a garment having a waist opening and two leg openings; and relaxing the chassis such that the garment will have laterally oriented contractive forces about the lower torso of the wearer.

While the disposable garment of the present invention may take many forms it preferably comprises an absorbent core positioned in the crotch region. The disposable garment preferably also comprises an outer cover which is loosely joined to the chassis to provide a garment-like appearance. In a particularly preferred embodiment the outer cover will be joined to the chassis such that the outer cover provides a skirt-like or shorts-like appearance.

BRIEF DESCRIPTION OF THE DRAWING

While the specification concludes with claims particularly pointing out and distinctly claiming the subject matter which is regarded as forming the present invention, it is believed that the invention will be better understood from the following description which is taken in conjunction with the accompanying drawings in which like designations are used to designate substantially identical elements, and in which:

DETAILED DESCRIPTION OF THE INVENTION

Figure 1:
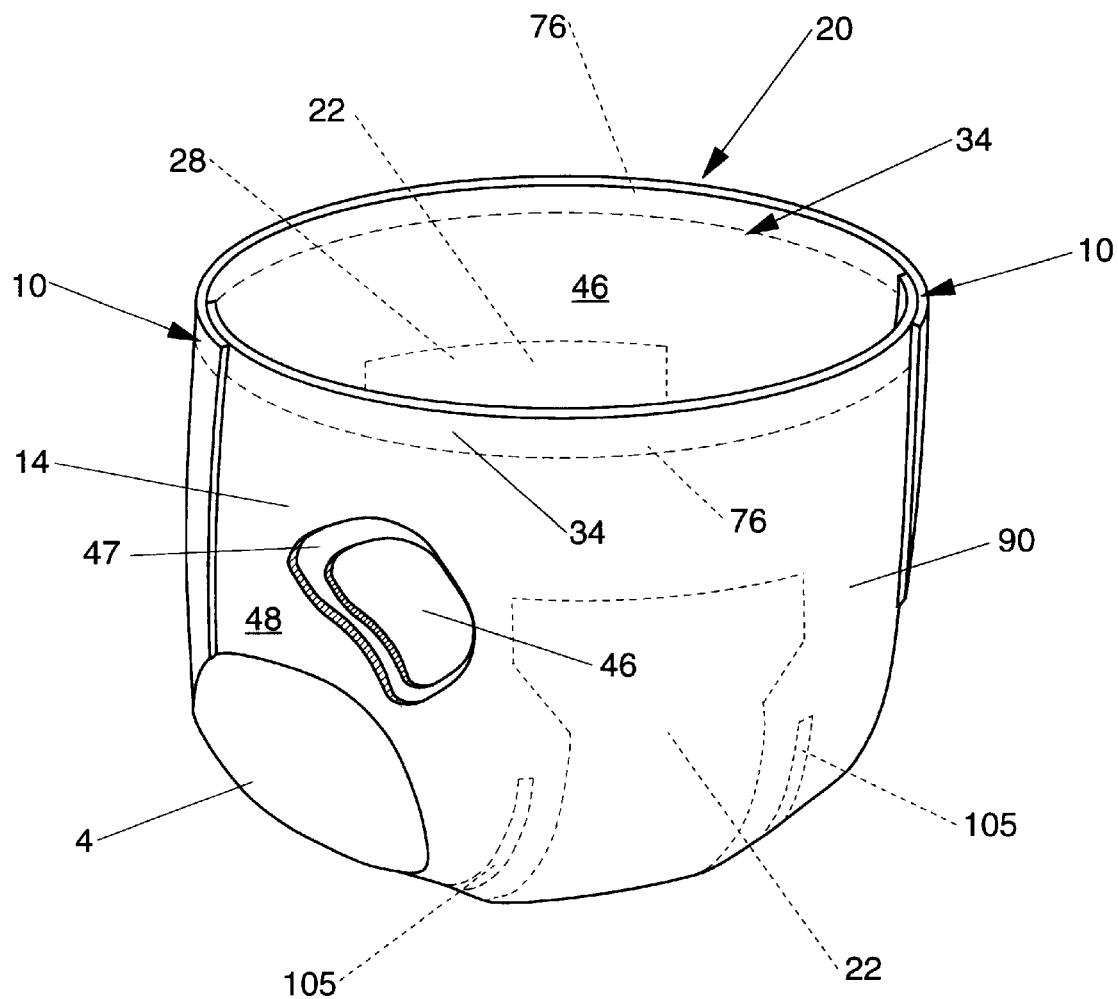
FIG. 1 is a perspective view of the disposable training pant embodiment of the present invention in a typical in-use configuration as it would be applied to a wearer.

Referring to the drawings, it will be noted that FIG. 1 is a perspective view of a disposable garment. A disposable garment is one which is intended to be discarded after it is used (i.e., it is not intended to be laundered or otherwise restored or reused). The disposable garment may be provided with an absorbent assembly which is placed in close proximity to the body of the wearer to absorb and contain the various exudates discharged from the body. A preferred embodiment of the disposable garment of the present invention, disposable training pants 20, is shown in FIG. 1. The training pants 20 of FIG. 1, comprise an elastomeric chassis 14, fixed side seams 10, and an absorbent assembly 22.

The chassis 14 is comprised of a laminate 90 which comprises an elastomeric adhesive lamina 47 joined in face-to-face relation with relatively inextensible outboard lamina 46, 48 which face outwardly and define the two opposed faces of the laminate 90. The outboard lamina 46, 48 are joined to the elastomeric lamina 47 while the elastomeric lamina 47 is prestretched in at least the lateral, or cross machine, direction. In a particularly preferred embodiment the elastomeric lamina will be a film of pressure sensitive adhesive and the gatherable laminae will be adhesively bonded to opposite sides of the pressure sensitive adhesive film by utilizing the pressure sensitive adhesive properties of the elastomeric lamina. As used herein, the terms "lateral direction" or "laterally" shall refer to the direction transverse to the direction transverse the longitudinal centerline l of an individual article. As used herein, the term "longitudinal direction" will refer to the direction parallel to the longitudinal centerline l of the chassis 14. As used herein, the term "cross machine direction" shall refer to the direction transverse to the machine direction of a moving web.

Figure 2:
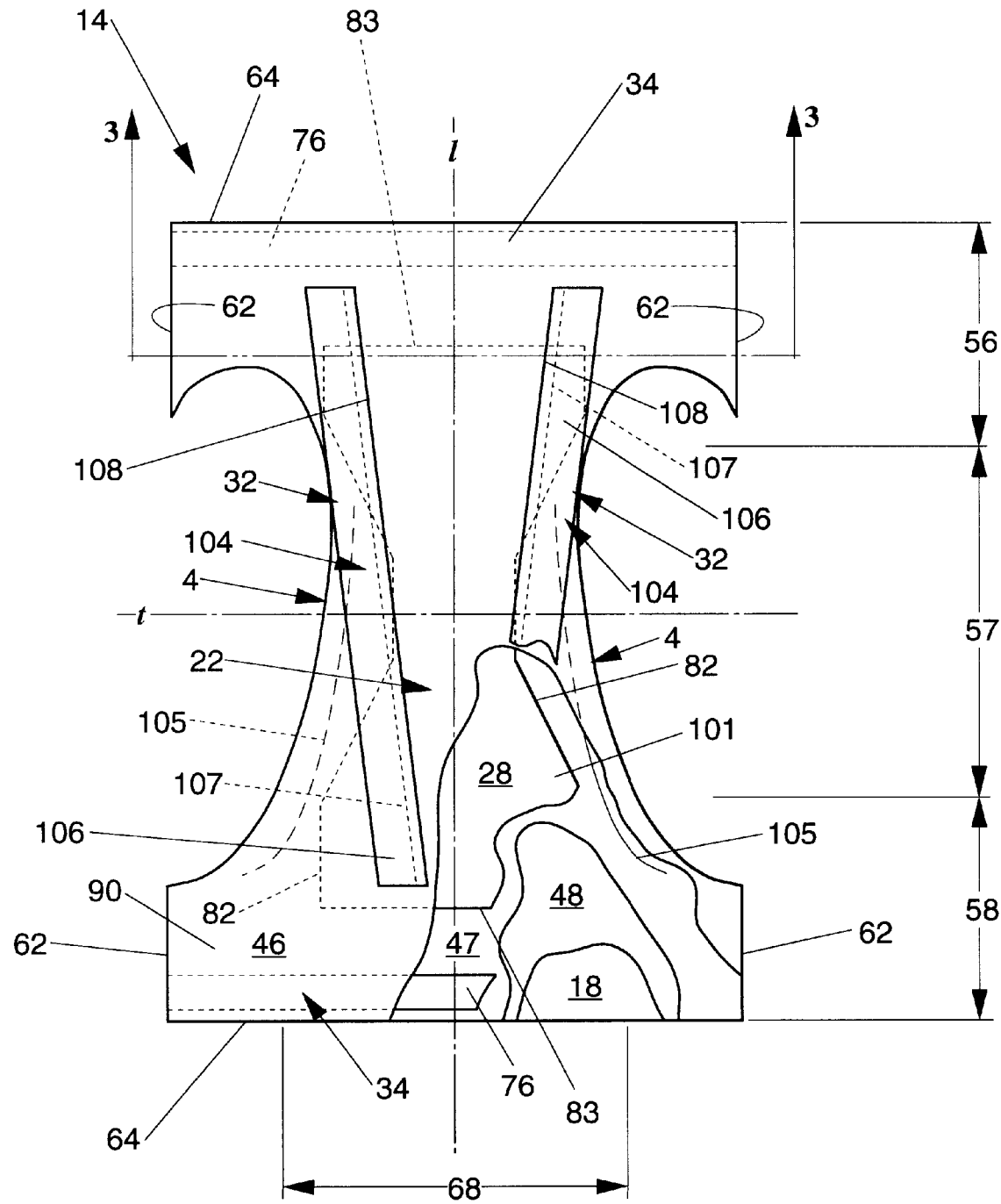
FIG. 2 is a top plan view of the chassis of the training pant embodiment of the present invention having portions cut away to reveal the underlying structure, the surface which will form the outer surface of the disposable garment facing away from the viewer.

FIG. 2 is a partially cut-away plan view of the disposable garment 20 of FIG. 1, prior to the front portion 56 and rear portion 58 of the chassis 14 being joined together at the side seams 10. FIG. 2 shows the elastomeric chassis 14 in its flat-out, uncontracted state. The chassis 14 of the present invention preferably has a symmetric, modified hour-glass shape. The chassis 14 will have at least a front portion 56, a rear portion 58, and a crotch portion 57. The chassis will comprise an elastomeric laminate 90 comprising at least two lamina, an elastomeric lamina joined to a gatherable lamina. Preferably, as shown in FIG. 2, the chassis 14 will comprise an outer lamina 48, an inner lamina 46 and an elastomeric lamina 47 joined between the inner and outer laminae 46 and 48. As will be discussed hereinbelow, the inner and outer laminae 46, 48 are preferably joined to the elastomeric lamina 47 while the elastomeric lamina 47 is in a laterally stretched condition such that the contractive forces of the chassis are oriented in the cross machine direction or perpendicular to the longitudinal centerline l of the chassis 14. Such laminates and methods of forming such laminates are discussed hereinbelow. In a particularly preferred embodiment, the chassis 14 may also comprise elastic waistband members 76, and elastic legband members 105 secured between the elastomeric lamina 47 and the inner lamina 46 or outer lamina 48, preferably the outer lamina 48.

The elastomeric lamina 47 will be elastomeric in at least the cross machine direction, preferably will be elastomeric in both the cross machine direction and the machine direction, and more preferably will be elastomeric in all directions. The elastomeric lamina 47 will also be compliant and non-irritating to the wearer's skin, and, at least the surface of the elastomeric lamina 47 will comprise a pressure sensitive adhesive. The elastomeric lamina 47 will preferably be a pressure sensitive, elastomeric adhesive. As used herein, a material which is "elastomeric", is capable of substantially recovering its size and shape after being stretched or elongated. As used herein, the term "adhesive" will refer to a material which is capable of bonding to another material by sticking, or adhering, to the surface of the other material. A "pressure sensitive adhesive" is an adhesive that is responsive to pressure, i.e., capable of adhering under the influence of pressure alone. As used herein, the term "elastically extensible" means able to be stretched, without rupture, from the free length at least about 50 percent, preferably at least about 100 percent, more preferably at least about 350 percent, held for about 15 seconds, and within about 5 minutes return to within about 10 percent of the free length upon release of the force which causes such elongation to occur.

Preferably, the elastomeric lamina 47 will be comprised of a thin film of an elastomeric, pressure sensitive adhesive, so that it may be readily joined to the inner lamina 46 and the outer lamina 47 to form a unitary laminate 90. The adhesive selected for the elastomeric lamina 47 should also be capable of elongation from about 50 to about 800 percent in one or two principle directions without rupture, more preferably to at least about 1,000 percent without rupture, not exhibit excessive necking or thinning when elongated, or exhibit excessive hysteresis or delamination upon cycling. Pressure sensitive elastomeric adhesive marketed by the Findley Adhesives Corporation of Wauwatosa, Wis. in under the tradename 198-338, has been found to be particularly well suited for this purpose. Other suitable elastomeric films include H2206, HS2206, or H2330 each of which is available from the Findley Adhesives Corporation.

The outer lamina 48 is that portion of the chassis 14 which will form the exterior of the chassis 14, i.e. face away from the wearer. The outer lamina 48 is compliant, soft feeling, and non-irritating to the wearer's skin. A suitable lamina may be manufactured from a wide range of materials, such as plastic films; or woven or non-woven webs of natural fibers (e.g. wood or cotton fibers), synthetic fibers (e.g. polyester or polypropylene fibers), or a combination of natural and synthetic fibers. If the outer lamina 48 is a film, it is preferred that the film be formed from a hot-melt material manufactured by the Findley Adhesives Corporation of Wauwatosa, Wisconsin and marketed as H2901. If the outer layer 48 is a nonwoven, a preferred nonwoven is "0.6 oz Unicorn" manufactured by Fiberweb North America of Simpsonville, S.C.

The inner lamina 46 is that portion of the chassis 14 which will form the interior of the chassis 14, and will contact at least the waist and legs of the wearer. The inner lamina is also compliant, soft feeling, and non-irritating to the wearer's skin. A suitable inner lamina 46 may be manufactured from a wide range of materials, such as plastic films; or woven or non-woven webs of natural fibers (e.g. wood or cotton fibers), synthetic fibers (e.g. polyester or polypropylene fibers), or a combination of natural and synthetic fibers. A suitable inner lamina is "0.6 oz Unicorn" manufactured by Fiberweb North America of Simpsonville, S.C.

As used herein, the term "joined" encompasses configurations whereby an element is directly secured to the other element by affixing the element directly to the other element, and configurations whereby the element is indirectly secured to the other element by affixing the element to intermediate member(s) which in turn are affixed to the other element. In a preferred embodiment of the present invention, the inner lamina 46 and the outer lamina 48 are indirectly joined together by directly joining them to the elastomeric lamina 47. The elastomeric lamina 47 of the chassis 14 is prestretched prior to joining of the inner and outer laminae 46, 48. After prestretching the elastomeric lamina 47, the pressure sensitive adhesive property of the elastomeric lamina 47 provides for continuous face-to-face joining of the elastomeric lamina 47. with the inner and outer laminae 46, 48. Upon release of the force which causes the prestretching of the elastomeric lamina 47, the resulting laminate 90 gathers or contracts in the direction of prestretching. The resulting laminate 90 will be elastically extensible to the limit of prestretching of the elastomeric lamina 47. If the laminate 90 is elongated beyond the amount of prestretch of the elastomeric lamina 47, the free length of the relatively inextensible inner and outer lamina 46, 48 will be exceeded. Therefore the elastomeric lamina 47 should be prestretched to at least the desired limit of elongation of the chassis 14.

If the elastomeric lamina 47 is prestretched in two principal directions, the resulting laminate 90 will contract in both such directions, proportional to the magnitude of prestretching in each principal direction. However, a laminate which is only extensible in the transverse or cross-machine direction has been found to work well for the chassis 14 of the present invention.

The chassis 14 of the disposable training pants 20 preferably further comprises elasticized leg cuffs 32 for providing improved containment of liquids and other body exudates. Each elasticized leg cuff 32 may comprise several different embodiments for reducing the leakage of body exudates in the leg regions. (The leg cuff can be and is sometimes also referred to as leg bands, side flaps, barrier cuffs, or elastic cuffs.) U.S. Pat. No. 3,860,003 entitled "Contractable Side Portions For a Disposable Diaper" issued to Buell on Jan. 14, 1975, describes a disposable diaper which provides a contractible leg opening having a side flap and one or more elastic members to provide an elasticized leg cuff (gasketing cuff). U.S. Pat. No. 4,909,803 entitled "Disposable Absorbent Article Having Elasticized Flaps" issued to Aziz and Blaney on Mar. 20, 1990, describes a disposable diaper having "stand-up" elasticized flaps (barrier cuffs) to improve the containment of the leg regions. U.S. Pat. No. 4,695,278 entitled "Absorbent Article Having Dual Cuffs" issued to Lawson on Sep. 22, 1987, describes a disposable diaper having dual cuffs including a gasketing cuff and a barrier cuff. U.S. Pat. No. 4,704,115 entitled "Disposable Waist Containment Garment" issued to Buell on Nov. 3, 1987, discloses a disposable diaper or incontinent garment having side-edge-leakage-guard gutters configured to contain free liquids within the garment. Each of these patents are incorporated herein by reference.

While each elasticized leg cuff 32 may be configured so as to be similar to any of the leg bands, side flaps, barrier cuffs, or elastic cuffs described above, it is preferred that each elasticized leg cuff 32 comprise a side flap 104 with one or more elastic strands 105, and a stand-up flap 106 with one or more elastic strands 107. In a preferred embodiment, the stand-up flap 106 will be oriented oblique to the longitudinal centerline l on the chassis 14. To provide improved leakage control and increased comfort to the wearer, the leg cuffs will preferably be "inflected", i.e., the distal ends 108 of the stand-up flaps 106 are closer together in the rear portion 58 than in the front portion 56, i.e., the stand-up flaps 106 diverge away from the longitudinal centerline l in at least the crotch portion 57 and the front portion 56. Inflected leg cuffs are described in greater detail in U.S. Pat. No. 5,087,255, entitled "Absorbent Article Having Inflected Barrier Cuffs" issued to Bret A. Sims on Feb. 11, 1992, which patent is incorporated herein by reference.

In a preferred embodiment, the leg openings 4, as shown in FIG. 2, will be non-symmetrical about the transverse centerline t l of the chassis 14, so that the finished garment, in its typical in-use configuration, will have a "French cut". As used herein, the term "French cut" will refer to leg openings that contact the body of the wearer at or above the low-motion zone of the wearer in the front of the garment, while fully covering the buttocks of the wearer in the rear. As used herein, the term "low-motion zone" shall refer to the areas where each leg meets the torso on the front of the wearer's body, and is generally defined by the crease formed on the front of the wearer's body when the wearer raises his/her leg.

The chassis 14 of the disposable training pants 20 further preferably comprises an elasticized waistband 34 disposed adjacent the end edge 64 of the disposable training pants 20 in at least the rear portion 58, and more preferably will also have an elasticized waistband 34 disposed in the front portion 56. The waistband of the disposable training pants 20 is that portion which is intended to be placed adjacent the wearer's waist. The elasticized waistband 34 provides a member that maintains a defined area coverage, contacts the wearer's waist, and is elastomeric in at least the lateral direction so as to dynamically fit against the waist of the wearer and to dynamically conform to the waist of the wearer so as to provide improved fit. Thus, the waistband is generally that portion of the disposable training pants 20 extending from the end edge 64 of the disposable training pants 20 to at least the waist edge 83 of the absorbent core 28. While the elasticized waistband 34 can comprise a separate element affixed to the chassis 14 of the disposable training pants 20, the waistband is preferably an extension of other elements of the disposable training pants 20 such as the laminae 46, 48, or any combination of these elements and an elastomeric material joined thereto. Alternatively, the topsheet 24 and the backsheet 26 of the absorbent assembly 22, may extend beyond the edges of the absorbent core 28 and have an elastomeric material joined thereto to form an elasticized waistband. Disposable training-pants are often constructed so as to have two elasticized waistbands; one positioned in the front portion 56 and one positioned in the rear portion 58. The disposable training pants 20 at least has an elasticized waistband 34 disposed in at least the central region 68 of the rear portion 58. Preferably, as shown in FIG. 2, another elasticized waistband is disposed in the front portion 56.

The elasticized waistband 34 may be constructed in a number of different configurations. In a preferred embodiment of the present invention shown in FIG. 2, the elasticized waistband 34 comprises an elastic waistband member 76 interposed between one of the gatherable laminae 46 or 48 and the elastomeric lamina 47 and operatively associated therewith to gather the front portion 56 and rear portion 58 of the disposable training pants 20. An example of such an elasticized waistband for use herein is the elasticized waistband disclosed in U.S. Pat. No. 4,515,595 entitled "Disposable Diapers With Elastically Contractible Waistbands", which issued to Kievit and Osterhage on May 7, 1985, and which patent is incorporated herein by reference.

Any suitable elastomeric material as known in the art may be used as the elastic waistband member 76 of the present invention. Examples of suitable elastomeric materials include elastomeric films, elastomeric foams such as polyurethane foams or crosslinked natural rubber foams; formed elastic scrim; elastomeric films such as heat shrinkable elastic materials; elastomeric film laminates such as a laminate of a heat-shrinkable elastomeric film and a resilient member; elastomeric stretch laminates such as "zero strain" stretch laminates as described hereinafter or mechanically stretched pretensioned stretch laminates; and elastic strands made from rubber, LYCRA, or other materials.

In a particularly preferred embodiment, the elastic waistband member 76 comprises a strip of elastomeric film which is laterally stretched and secured to the elastomeric lamina 47 while the elastomeric member is in a laterally stretched condition. An elastomeric film suitable for use as the elastic waistband member 76 is available from Findley Adhesives Corporation of Wauwatosa, Wis., and marketed under the trade name Findley 198-338. Other suitable elastomeric films include H2206, HS2206, or H2330 each of which is available from the Findley Adhesives Corporation.

Preferably, the training pants 20 will also comprise an outer cover 18 partially bonded to the chassis 14. As used herein, the term "partially bonded" will be understood to mean that only portions of the mutually facing surfaces of two materials are bonded together, i.e., the two materials are not bonded together over 100% of their mutually facing surfaces. Likewise, the term "wholly bonded", as used herein, will be understood to mean that the mutually facing surfaces of two materials are completely bonded together, i.e., the materials are bonded together over 100% of their mutually facing surfaces. Preferably, the outer cover 18 is bonded to the chassis 14 peripheral areas of the chassis 14. As used herein, the terms "periphery" or "peripheral areas" shall refer to the portion of material adjacent to the boundary edges. For example, the periphery of the chassis 14 is that portion of the chassis adjacent to the end edges 64 and longitudinal side edges 62. In a particularly preferred embodiment, the central area 17 of the outer cover 18 will be bloused from the central area 17 of the chassis 14. The central area 17 is that portion of the outer cover or chassis which is inboard of the periphery or peripheral areas. As used herein, the term "bloused" shall be understood to mean that portions of a first layer of material are unattached and loosely fitted to a second layer of material, i.e., the first layer of material hangs or has been caused to hang loose and full from the second layer of material to which it is joined.

The loosely fitted outer cover 18 hides or substantially masks the underlying elastomeric chassis from a viewer and provides the absorbent article with a garment-like appearance. In a preferred embodiment, the loosely fitted outer cover will be provided with a printed pattern to further mask the underlying chassis from view. Disposable absorbent articles having such bloused outer covers are discussed in greater detail in commonly assigned, co-pending U.S. patent application Ser. No. 14 08/176,055, (P&G Case 5125), entitled "Garment-like Disposable Absorbent Article Having A Bloused Outer Cover", filed concurrently herewith in the names of Margaret H. Hasse and Patrick J. Allen, which patent application is incorporated herein by reference.

Blousing of the outer cover 18 may be accomplished by providing an oversized outer cover 18 and joining the peripheral edges of the oversized outer cover 18 to the peripheral edges of the chassis 14. As used herein, the term "oversized outer cover" will refer to an outer cover which is longer (longitudinally) and/or wider (laterally) than the chassis 14 in its relaxed, unstretched condition.

SIDE SEAMS

The side seams 10 of the training pants 20 may be formed by any means well known in the art. For example, the seams may be sewn, adhesively bonded, ultrasonically bonded, heat sealed, or the like. Methods of forming side seams on disposable absorbent articles, such as training pant, are discussed in U.S. Pat. No. 4,205,679 issued to Repke, et al.; U.S. Pat. No. 4,335,425 issued to Jones, et al.; U.S. Pat. No. 4,610,680 issued to LaFleur, et al.; U.S. Pat. No. 4,619,649 issued to Roberts.; U.S. Pat. No. 4,747,846 issued to Boland, et al. ; U.S. Pat. No. 4,641,381 which issued to Heran, et al. ; U.S. Pat. No. 4,610,681 issued to Strohbeen, et al. ; U.S. Pat. No. 4,909,804 issued to Douglas, Sr.; U.S. Pat. No. 5,074,854 issued to Davis; and U.S. Pat. No. 5,236,430 issued to Russell P. Bridges; which patents are incorporated herein by reference.

In a preferred embodiment, the side seam 10 will be formed by bonding the front portion to the rear portion in an overlapping configuration such as is shown in FIG. 1. The front portion and the rear portion may be bonded in an overlapping configuration using any of the bonding methods commonly known in the art. For example, the front portion and the rear portion may be adhesively bonded, ultrasonically bonded, heat sealed, bonded using pressure and/or heat, or the like. Preferably, the front portion and the rear portion are adhesively bonded in an overlapping configuration. In a particularly preferred embodiment, the elastomeric lamina 47 of the chassis 14 will have a portion left exposed (i.e., not covered by or joined to the inner lamina 46 and/or the outer lamina 48), and the exposed adhesive surface of the elastomeric lamina 47 is used to secure the front portion 56 and the rear portion 58 in an overlapping configuration.

Although the seams of the disposable article of the present invention have been shown and described herein as being fixed seams, i.e., non-reusable seams, the disposable absorbent article of the present invention may be provided with seams which allow the article to be opened and re-closed. Seams which allow disposable absorbent articles to be opened and re-closed are well known in the disposable diaper art. A "disposable diaper" is a particular disposable article worn by infants or incontinent persons, which is drawn between the legs, and fastened about the waist of the wearer. These types of seams generally comprise tape tabs joined to the front portion or the rear portion of the article. These tape tabs are provided with an adhesive or mechanical fastening means capable of securing the rear portion and front portion in an overlapping configuration about the lower torso of the wearer, and allow the article to be opened and re-closed. Such fastening systems are described in detail in U.S. Pat. No. 3,848,594 issued Nov. 19, 1974 to Buell; U.S. Pat. No. 4,699,622 issued Oct. 13, 1987 to Toussant et al.; and U.S. Pat. No. 4,846,815 issued Jul. 11, 1989 to Scripps; all of which are incorporated herein by reference.

ABSORBENT ASSEMBLY

The training pants 20 will preferably also comprise an absorbent assembly 22. The absorbent assembly 22 is any absorbent means which is generally compressible, conformable, non-irritating to the wearer's skin, and capable of absorbing and retaining liquids such as urine and other certain body exudates. The absorbent assembly 22 of the disposable training pants 20 may be an insert, i.e. an element formed separately from the chassis and inserted therein. Alternatively and preferably, the absorbent assembly 22 will be an absorbent element disposed between the elastomeric lamina 47 and the inner lamina 46.

The absorbent assembly 22 of the disposable training pants 20 preferably comprises at least an absorbent core 28. The absorbent core 28 may be any absorbent means which is generally compressible, conformable, non-irritating to the wearer's skin, and capable of absorbing and retaining liquids such as urine and other certain body exudates.

The absorbent core 28 may be manufactured in a wide variety of sizes and shapes (e.g., rectangular, hourglass, "T"-shaped, asymmetric, etc.) and from a wide variety of liquid-absorbent materials commonly used in disposable diapers and other absorbent articles such as comminuted wood pulp which is generally referred to as airfelt. Examples of other suitable absorbent materials include creped cellulose wadding, meltblown polymers including coform, cross-linked cellulosic fibers, tissue including tissue wraps, absorbent foams, absorbent sponges, superabsorbent polymers, absorbent gelling materials, or any equivalent material or combinations of materials. The configuration and construction of the absorbent core may also be varied (e.g., the absorbent core may have varying caliper zones, a hydrophilic gradient, a superabsorbent gradient, or lower average density and lower average basis weight acquisition zones; or may comprise one or more layers or structures). The total absorbent capacity of the absorbent core 28 should, however, be compatible with the design loading and the intended use of the disposable garment 20. Further, the size and absorbent capacity of the absorbent core 28 may be varied to accommodate wearers ranging from infants through adults.

A preferred embodiment of the absorbent assembly 22 has a modified hour glass-shape absorbent core 28 which is symmetric about the longitudinal centerline 1. While a preferred embodiment of the absorbent assembly 22 has a modified hourglass-shaped absorbent core 28, it should be understood that the size, shape, configuration and total absorbent capacity of the absorbent core 28 may be varied to accommodate wearers ranging from infants to adults. Therefore, the dimensions, shape and configuration of the absorbent core may be varied (e.g., the absorbent core may have a varying caliper, or a hydrophilic radiant, or may or may not contain absorbent gelling materials). An exemplary absorbent structure for use as the absorbent core 28 of the present invention that has achieved wide acceptance and commercial success is described in U.S. Pat. No. 4,610,678 entitled "High-Density Absorbent Structures" issued to Weisman and Goldman on Sep. 9, 1986. U.S. Pat. No. 4,673,402 entitled "Absorbent Articles With Dual-Layered Cores" issued to Weisman, Houghton, and Gellert on Jun. 16, 1987; U.S. Pat. No. 4,888,231 entitled "Absorbent Core Having A Dusting Layer" issued to Angstadt on Dec. 19, 1989; and U.S. Pat. No. 4,834,735, entitled "High Density Absorbent Members Having Lower Density and Lower Basis Weight Acquisition Zones", issued to Alemany et al. on May 30, 1989; also describe absorbent structures that are useful in the present invention. Each of these references are incorporated herein by reference.

The absorbent core 28 is preferably a batt of airfelt and particles of absorbent, gelling material, about 13 centimeters (5 inches) wide (lateral dimension), about 34 centimeters (13.5 inches) long (longitudinal dimension) and approximately 5 centimeters (2 inches) across the narrowest part of the crotch portion 57. Preferably, the portion of the absorbent core that will be generally located in the front portion 56 and crotch portion 57 will have a higher basis weight than the portion of the absorbent core that will be generally located in the rear portion 58. More preferably, the portion of the absorbent core that will be generally located in the front portion 56 and crotch portion 57 will have a basis weight three times the basis weight of the portion of the absorbent core that will be generally located in the rear portion 58. In a preferred embodiment of the absorbent core 28, about 25.4 centimeters of the absorbent core's length will be generally located in the front portion 56 and crotch portion 57 and will have a basis weight of about 0.69 grams per square inch, and 11.4 centimeters of the absorbent core's length will be generally located in the rear portion 58 and will have a basis weight of about 0.23 grams per square inch.

In a particularly preferred embodiment, the absorbent core 28 will be a batt comprising 6 grams of absorbent gelling material, 3 grams of polyester fibers, and 12 grams of absorbent cellulose, and will have a substantially uniform basis weight.

As shown in FIG. 2, the absorbent assembly 22 preferably comprises an absorbent core 28 positioned between the elastomeric lamina 47 and the inner lamina 46 of the chassis 14. Thus, the inner lamina 46 will function as a "topsheet" and the elastomeric lamina 47 will function as a "backsheet". When the inner lamina 46 is used as a topsheet as described herein, the inner lamina 46 may be made of a hydrophilic material comprising about 20% to about 30% rayon so as to feel wet and signal a discharge of urine to a toilet training child. The absorbent core 28 is preferably positioned adjacent the elastomeric lamina 47 and is preferably joined thereto by the contacting the adhesive surface of the elastomeric lamina 47. Alternatively, the absorbent assembly may be joined thereto by attachment means such as those well known in the art. Suitable attachment means are described herein with respect to joining the backsheet 26 of the absorbent insert 41 to the absorbent core 28.

Figure 3:
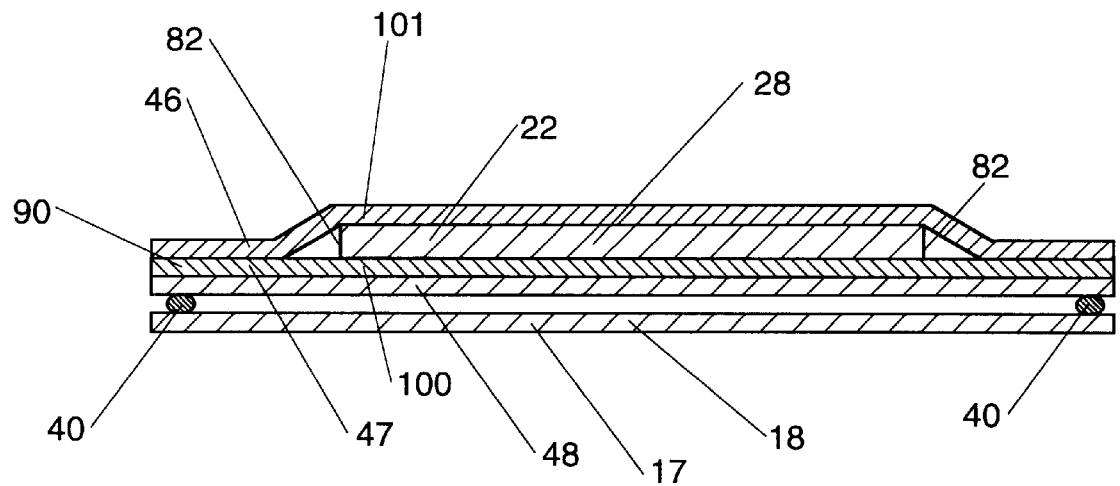
FIG. 3 is a cross-sectional view of the chassis shown in FIG. 2 taken along section line 3—3 of FIG. 2 with leg cuffs removed.

Referring to FIG. 3, the absorbent core 28 has a garment surface 100, a body surface 101, side edges 82 and end edges 83. The elastomeric lamina 47 is positioned adjacent the garment surface 100 of the absorbent core 28 and is preferably joined thereto by the adhesive nature of the pressure sensitive elastomeric adhesive film 47. The elastomeric adhesive lamina 47 is impervious to liquids (e.g., urine) and, as discussed herein, is preferably manufactured from a thin, elastomeric film of pressure sensitive adhesive. The elastomeric lamina 47 will prevent the exudates absorbed and contained in the absorbent core 28 from wetting articles which contact the disposable training pants 20 such as bed sheets and garments.

a. ABSORBENT ASSEMBLY AS AN INSERT

Figure 4:
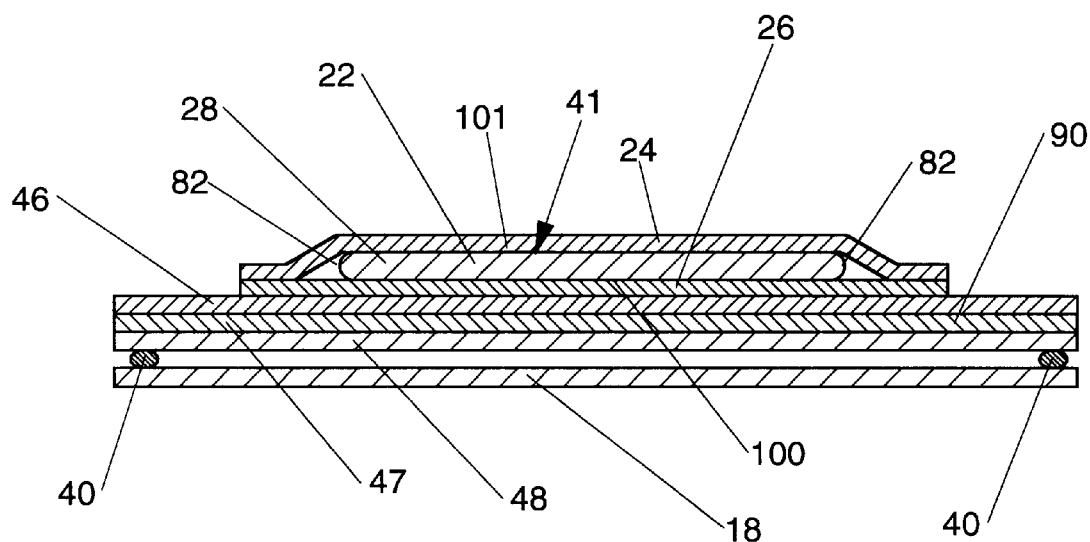
FIG. 4 is a fragmentary sectional view of the chassis of an alternate embodiment of the present invention.

As shown in FIG. 4, the absorbent assembly 22 of the disposable training pants 20 may comprise an absorbent insert 41, which is manufactured separately from the chassis 14 and is secured to the inner lamina 46. The absorbent insert 41 will preferably comprises at least an absorbent core 28 and an outer covering layer comprising a topsheet 24 and a backsheet 26. The absorbent insert 41 is preferably positioned adjacent the inner surface of the chassis 14, i.e., adjacent the inner lamina 46 and is preferably joined thereto by attachment means such as those well known in the art. Suitable attachment means are described hereinbelow with respect to joining the backsheet 26 to the absorbent core 28.

As shown in FIG. 4, the backsheet 26 of the absorbent inert 41 is positioned adjacent the garment surface 100 of the absorbent core 28 and is preferably joined thereto by attachment means (not shown) such as those well known in the art. For example, the backsheet 26 may be secured to the absorbent core 28 by a uniform continuous layer of adhesive, a patterned layer of adhesive, or ah array of separate lines, spirals, or spots of adhesive. Adhesives which have been found to be satisfactory are manufactured by Century Adhesives, Inc. of Columbus, Ohio and marketed as Century 5227; and by H. B. Fuller Company of St. Paul, Minn. and marketed as HL-1258. The attachment means will preferably comprise an open pattern network of filaments of adhesive as is disclosed in U.S. Pat. No. 4,573,986 entitled "Disposable Waste-Containment Garment", which issued to Minetola and Tucker on Mar. 4, 1986, and which is incorporated herein by reference. An exemplary attachment means of an open pattern network of filaments comprises several lines of adhesive filaments swirled into a spiral pattern such as is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Each of these patents are incorporated herein by reference. Alternatively, the attachment means may comprise heat bonds, pressure bonds, ultrasonic bonds, dynamic mechanical bonds, or any other suitable attachment means or combinations of these attachment means as are known in the art.

The backsheet 26 of the absorbent insert 41 is impervious to liquids (e.g., urine) and is preferably manufactured from a thin plastic film, although other flexible liquid impervious materials may also be used. As used herein, the term "flexible" refers to materials which are compliant and will readily conform to the general shape and contours of the human body. The backsheet 26 prevents the exudates absorbed and contained in the absorbent core 28 from wetting articles which contact the disposable training pants 20 such as bed sheets and garments. The backsheet 26 may thus comprise a woven or nonwoven material, polymeric films such as thermoplastic films of polyethylene or polypropylene, or composite materials such as a film-coated nonwoven material. Preferably, the backsheet is a film having a thickness of from about 0.012 mm (0.5 mil) to about 0.051 mm (2.0 mils).

The size of the backsheet 26 is dictated by the size of the absorbent core 28 and the exact disposable garment design selected. In a preferred embodiment, the backsheet 26 will wrap around at least the absorbent core and possibly over the edge portions of the topsheet 24 in at least the crotch portion 57, so that the elasticized leg cuff 32 will be free from any backsheet material, and, thus, are not inhibited by the backsheet material. Alternatively, the topsheet 24 may wrap around the core and under the edge portions of the backsheet 26 in at least the crotch portion 57, or the topsheet 24 and backsheet 26 may be "side-notched" in the crotch portion 57 so that the elasticized leg cuffs 32 are not inhibited by the backsheet material.

The topsheet 24 of the absorbent insert 41 is positioned adjacent the body surface 101 of the absorbent core 28 and is preferably joined thereto and to the backsheet 26 by attachment means (not shown) such as those well known in the art. Suitable attachment means are described with respect to joining the backsheet 26 to the absorbent core 28. In a preferred embodiment of the present invention, the topsheet 24 and the backsheet 26 are joined directly to each other in the areas extending beyond the absorbent core 28 and are indirectly joined together by directly joining them to the absorbent core 28 by the attachment means (not shown).

The topsheet 24 of the absorbent insert 41 is compliant, soft feeling, and non-irritating to the wearer's skin. Further, the topsheet 24 is liquid pervious permitting liquids (e.g., urine) to readily penetrate through its thickness. A suitable topsheet may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. The topsheet 24 may be made of hydrophilic material comprising about 20% to 30% rayon so as to feel wet and signal a discharge of urine to a toilet training child.

There are a number of manufacturing techniques which may be used to manufacture the topsheet 24. For example, the topsheet 24 may be a nonwoven web of fibers. When the topsheet comprises a nonwoven web, the web may be spunbonded, carded, wet-laid, meltblown, hydroentangled, combinations of the above, or the like. A preferred topsheet is carded and thermally bonded by means well known to those skilled in the fabrics art.

While in a preferred embodiment of the present invention, the disposable article comprises an absorbent assembly (either as part of the chassis 14, or an insert joined to the chassis 14), the disposable article may be made without an absorbent assembly 22. Such an embodiment would function as a disposable undergarment not intended to absorb bodily discharges.

METHOD OF MAKING THE ELASTOMERIC LAMINATE

Figure 6:
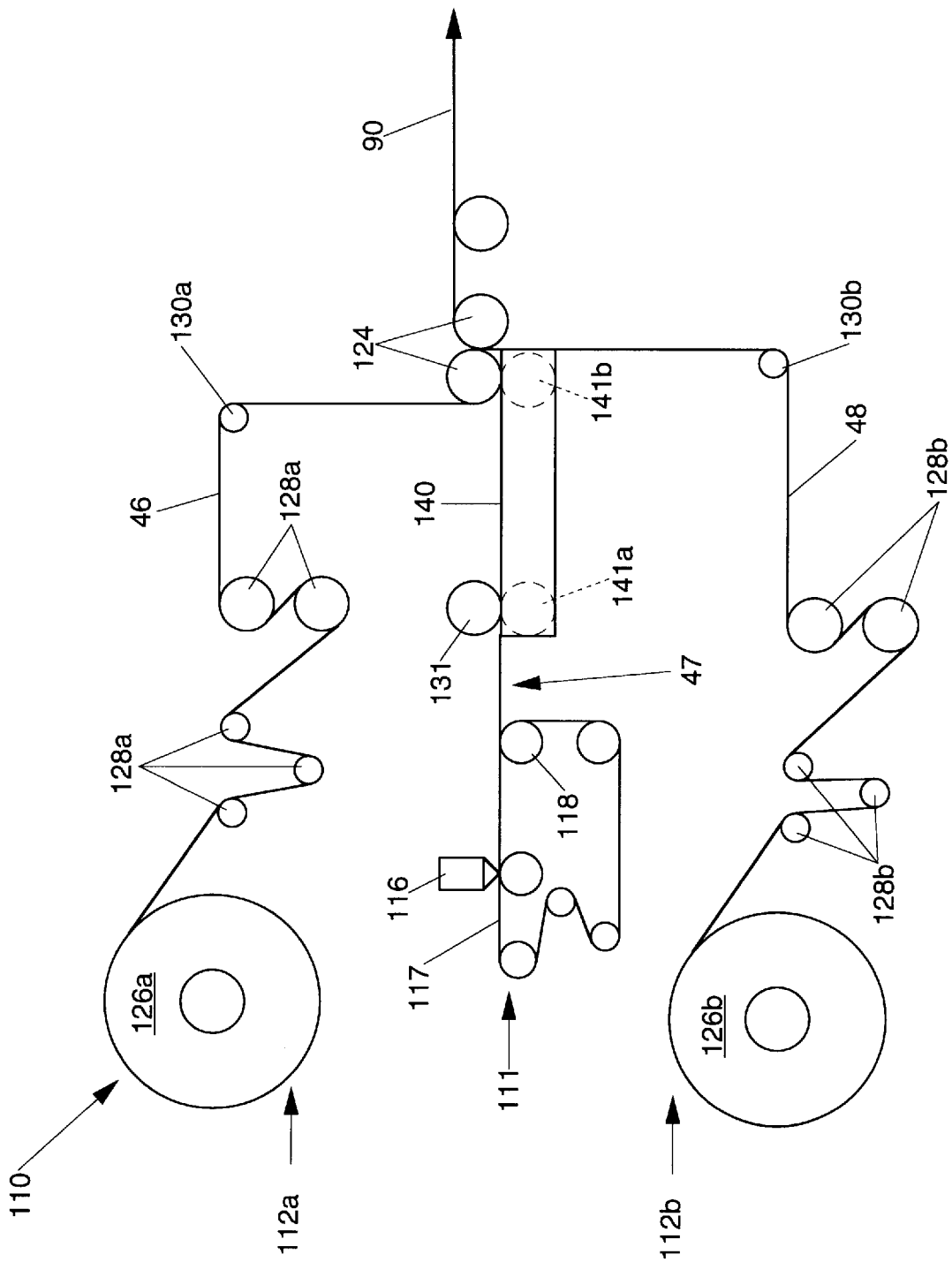
FIG. 6 is a side elevational schematic view of one apparatus which may be used to produce the elastomeric laminate of the present invention.
Figure 7:
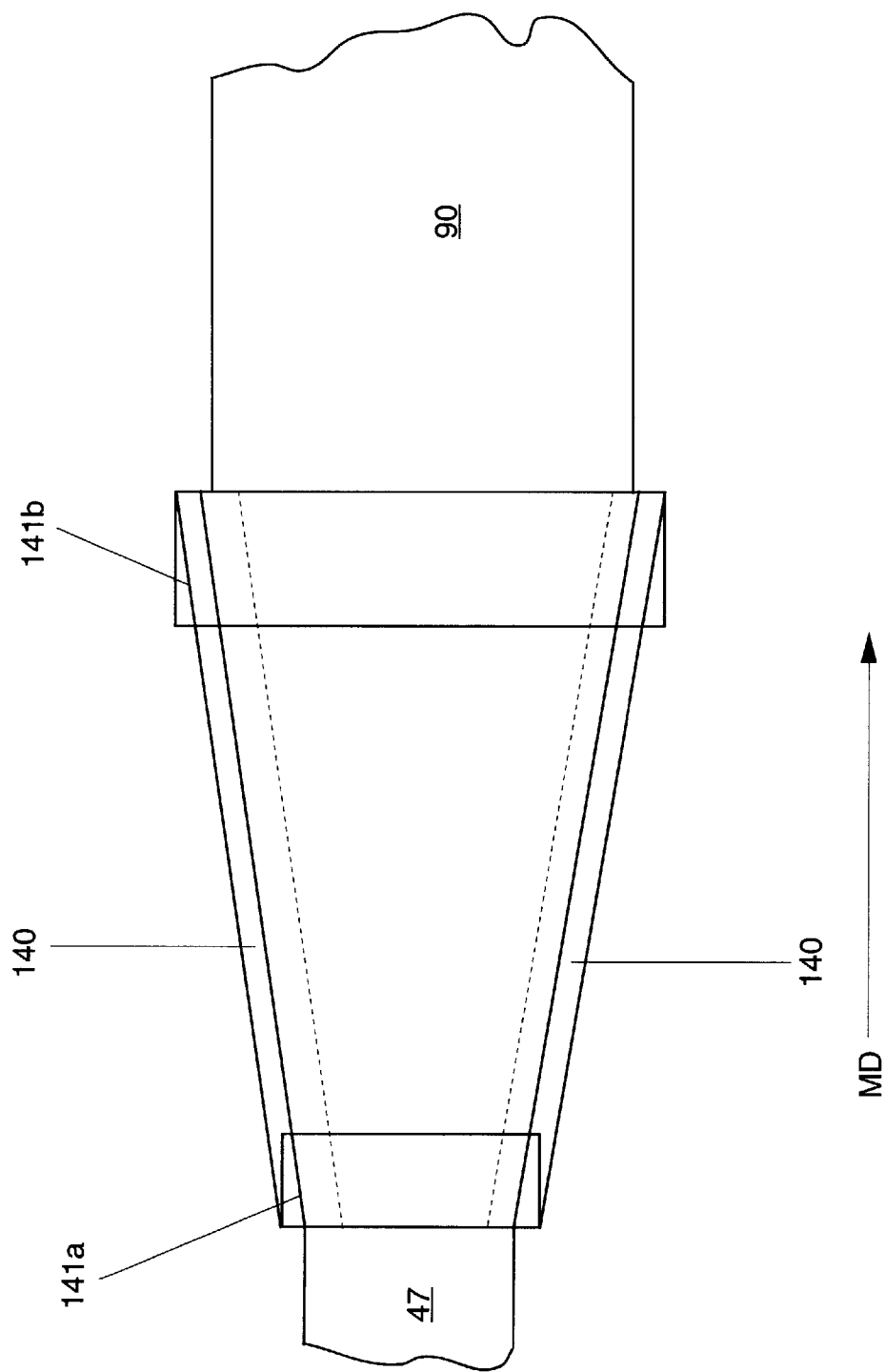
FIG. 7 is a top plan view of the diverging belts of the apparatus shown in FIG. 6.

Referring to FIGS. 6 and 7, the elastomeric laminate 90 of the present invention may be produced on the illustrated apparatus 110. The apparatus 110 comprises three separate lines, line 111 for the elastomeric lamina 47, and complementary lines 112a and 112b for the outboard laminae 46, 48 respectively.

The first line 111, utilized for the elastomeric lamina 47 comprises an extrusion head 116; a forming belt; and a chill roll 118; to form the web of the elastomeric lamina 47. The application roll 131 applies the longitudinal edges of the elastomeric lamina 47 web to the diverging belts 140 which laterally stretch the elastomeric lamina 47 as it moves forwardly. The outboard laminae 46, 48 are taken from unwind rolls 126a and 126b, passed through tensioning rolls 128a and 128b and through guide rolls 130a and 130b. As the elastomeric lamina 47 reaches the end of the diverging belt 140, the elastomeric lamina 47 is lifted off the diverging belts 140 by one of the combining rolls 124 and passes through the nip formed between the combining roll 124 along with the outboard laminae 46, 48 which are joined to opposite sides of the elastomeric lamina 47 to form a unitary laminate 90. After the laminate 90 leaves the nip of the combining rolls 124, the additional elements which make up the disposable article 20, i.e., topsheet, backsheet, waistband elastics, and legband elastics may be applied to the web. The laminate web 90 with the additional elements joined thereto may then be cut into individual articles, folded in the crotch portion 57, and seamed along the longitudinal edges to form a disposable absorbent article.

Examining FIGS. 6 and 7 in greater detail, the extrusion head 116 has a slot through which the molten elastic adhesive of the elastomeric lamina 47 is extruded to form a thin film of about 0.03 to about 1.0 millimeters (0.001–0.04 inches) in thickness, and of any desired width, onto the chill roll 188. An elastomeric lamina 47 of about 8.4 grams per square centimeter is suitable. An elastomeric lamina having a thickness of about 0.13 to about 0.38 millimeters (0.005–0.015 inches) is particularly preferred. Generally a thicker elastomeric lamina 47 is preferred as the thickness and stiffness of either outboard lamina 46, 48 increases. It will be apparent to one skilled in the art that increasing the thickness if the elastomeric lamina 47 will provide a proportional increase in the ultimate contact force of the laminate 90 of the chassis 14.

The extrusion head 116 extrudes the molten adhesive onto the forming belt 117 which transports the extruded adhesive to the chill roll 118. The chill roll 118 cools the extruded adhesive of the elastomeric lamina 47 into a web suitable for further processing. If desired, a second roll (not shown) may be utilized in conjunction with the chill roll 118 to provide additional cooling and a nip for compression of the web of the elastomeric lamina 47. If desired, the forming belt 117 may also cool the extruded adhesive The web of the elastomeric lamina 47 is separated from the forming belt 117 at the chill roll by a doctor blade 120 and is fed to the diverging belts 140.

If desired, the elastomeric lamina 47 may be drawn through the nip formed between a pair of tensioning rolls (not shown). The tensioning rolls provide for longitudinally stretching the elastomeric lamina 47 prior to being applied to the diverging belts. The tensioning roll would provide a laminate which is elastically extensible in two directions, i.e., the machine direction and the cross machine direction. A laminate which is elastically extensible in the machine direction (or longitudinal direction) and method of forming such a laminate are described in greater detail in U.S. Pat. No. 5,032,120, entitled "Disposable Absorbent Article Having Improved Leg Cuffs", issued Jul. 16, 1991 to Mary E. Freeland and Patrick J. Allen, which is incorporated herein by reference.

After being removed from the forming belt 117, the elastomeric lamina 47 is fed to the diverging belts 140 which will laterally stretch the elastomeric lamina 47 as it is transported forwardly. The diverging belts 140 are driven by any driving means well known in the art and are not driven by the adhesive film 47. Each belt 140 travels continuously about a pair of terminal rollers 141a, 141b. Each belt 140 has a substantially flat outer surface or working surface. The "outer surface" or "working surface" refers to the side of the belt which faces away from the terminal rollers and to which the edges of the adhesive film are removably adhered. Because of the adhesive nature of the elastomeric lamina 47, it is only necessary that about ¼ inch to about ¾ inch of the edges of the elastomeric lamina 47 be secured to the working surface of each belt 140. The belts 140 will be capable of traveling about the terminal rollers 141a, 141b, and may be comprised of any material to which the adhesive film 47 will adhere sufficiently in shear to laterally stretch the adhesive film 47, and from which the adhesive film 47 can be removed. Preferably, at least the working surface of the belts 140, are comprised of TEFLON. A suitable belt for use as the diverging belt of the present invention, is available from F. M. Sheppard & Co. of Erlanger, Ky. and is sold as Belt Style No. 3W11-2A The application roll 131 guides the longitudinal edges of adhesive film 47 onto the working surface of the belts 140. Referring to FIG. 7, as the belts 140 transport the adhesive film 47 in the machine direction (represented by the arrow labeled MD), the elastomeric lamina 47 is laterally elongated. This causes prestretching of the elastomeric lamina 47 in the cross machine direction. The adhesive film 47 is laterally stretched, i.e., stretched in the cross machine direction, as the diverging belts 140 move the adhesive film 47 forwardly in the direction of travel. FIG. 7 is a top plan view of a portion of the apparatus of FIG. 6, showing the diverging belts 140 traveling about the terminal rollers 141a and 141b. The application roll 131, line 112a, and combining rolls 124 are omitted from FIG. 7 for clarity.

The outboard laminae 46, 48 are taken form the unwind rolls 126a and 126b and preferably pass through the S-wrap tensioning roll 128a and 128b to provide for proper tensioning and prevent puckering or bunching of the outboard laminae 46, 48. Guide rolls 130a and 130b guide the webs of outboard laminae 46, 48 into the combining rolls 124. If necessary, a tracking system, not shown, as is commonly utilized and known in the art, may be employed in either or both lines 112a and 112b to optimally track and adjust the webs of outboard laminae 46, 48 into the combining rolls 124. A tracking system manufactured by the Fife Corporation of Oklahoma City, Okla., and sold as Model No. Op6 LRA may be suitable.

The laminae 46, 47, and 48 enter the combining rolls 124 and pass through the nip formed therebetween. The nip of the combining rolls 124 compresses the laminae 46, 48 into superposing contacting relationship with the opposed faces of the elastomeric lamina 47, causing the pressure sensitive adhesive of the elastomeric lamina 47 to bond to the outboard laminae 46, 48—joining the three laminae 46, 47, 48 to form elastomeric laminate 90. As used herein, the term "superpose" or "superposing" will refer to one layer of material having a particular geometric shape being laid upon another layer of material having a substantially similar geometric shape such that all like parts of the two layers of material substantially coincide. When the elastomeric laminate 90 is relaxed and the elastomeric lamina 47 is allowed to contract, the outboard lamina 46, 48 will become gathered in at least the transverse or lateral direction, which will form longitudinally extending, rugosities and the elastomeric lamina 90 will be laterally elastically extensible (i.e., elastically extensible in the cross machine direction). The elastomeric laminate 90 will be elastically extensible in the lateral direction up to about the free length of the outboard laminae 46, 48. As used herein, the term "rugosities" shall refer to small ridges, wrinkles, or furrows, i.e., long narrow indentations, in the surface of the laminate 90.

If desired, the laminate 90 need not incorporate two outboard laminae 46, 48. If desired, either or both outboard laminae may be omitted from the laminate 90. Such a structure may be manufactured by selectively not operating the line 112a or 112b of the outboard lamina, inner lamina 46 or outer lamina 48, desired to be omitted. The resulting laminate 90 would have one outboard lamina, inner lamina 46 or outer lamina 48, joined to elastomeric lamina 47.

After a two laminae laminate exits the nip of the combining rolls 124, the exposed face of the elastomeric lamina 47 may be deactivated, by blocking as is commonly known in the art, so that the adhesive of the elastomeric lamina 47 does not bond to other materials through the pressure sensitive properties of the adhesive of the elastomeric lamina 47. Blocking is accomplished by an adhesive deactivation system (not shown) applying a powder of resin to the exposed face of the elastomeric lamina 47. Suitable resin powders include talcum powder, polyolefinic powders, and preferably a resin similar to that used for the outboard lamina, inner lamina 46 or outer lamina 48. If desired, the adhesive deactivation system may be applied to the exposed face of the elastomeric lamina prior to the elastomeric lamina 47 entering the nip if the combining rolls 124.

Alternatively, the exposed face of the elastomeric lamina 47 may be deactivated by applying a non-adhesive elastomeric film thereto. A suitable non-adhesive elastomeric film is H2901 manufactured by Findley Adhesives Findley Adhesives Corporation of Wauwatosa, Wis.

If desired, the inner lamina 46 and/or the outer lamina 48 may be elastically extensible. The inner lamina and the outer lamina 48 may of similar of different materials, as desired. It will be apparent to one skilled in the art that an adhesive deactivation system should not be employed prior to the combining rolls 124 if a laminate 90 having two outboard laminae 46, 48 is to be constructed using the apparatus 111 of FIGS. 6 and 7.

The elastomeric laminate 90 is useful for many different purposes. For example, the laminate 90 may be used to form an elastomeric waistband; low pressure bandages, i.e., medical dressings or wraps; disposable elastomeric sweat bands to be worn on the wrists and/or forehead; disposable outergarments; and receiving surfaces or a landing zone for a mechanical fasteners; or the like.

METHOD OF MAKING THE ELASTOMERIC DISPOSABLE GARMENT

The elastomeric laminate 90 is also used for forming the chassis 14 of the disposable absorbent article of the present invention. To form the disposable absorbent article of the present invention, the laminate 90 is further processed after leaving the nip of the combining rolls 124.

Figure 8:
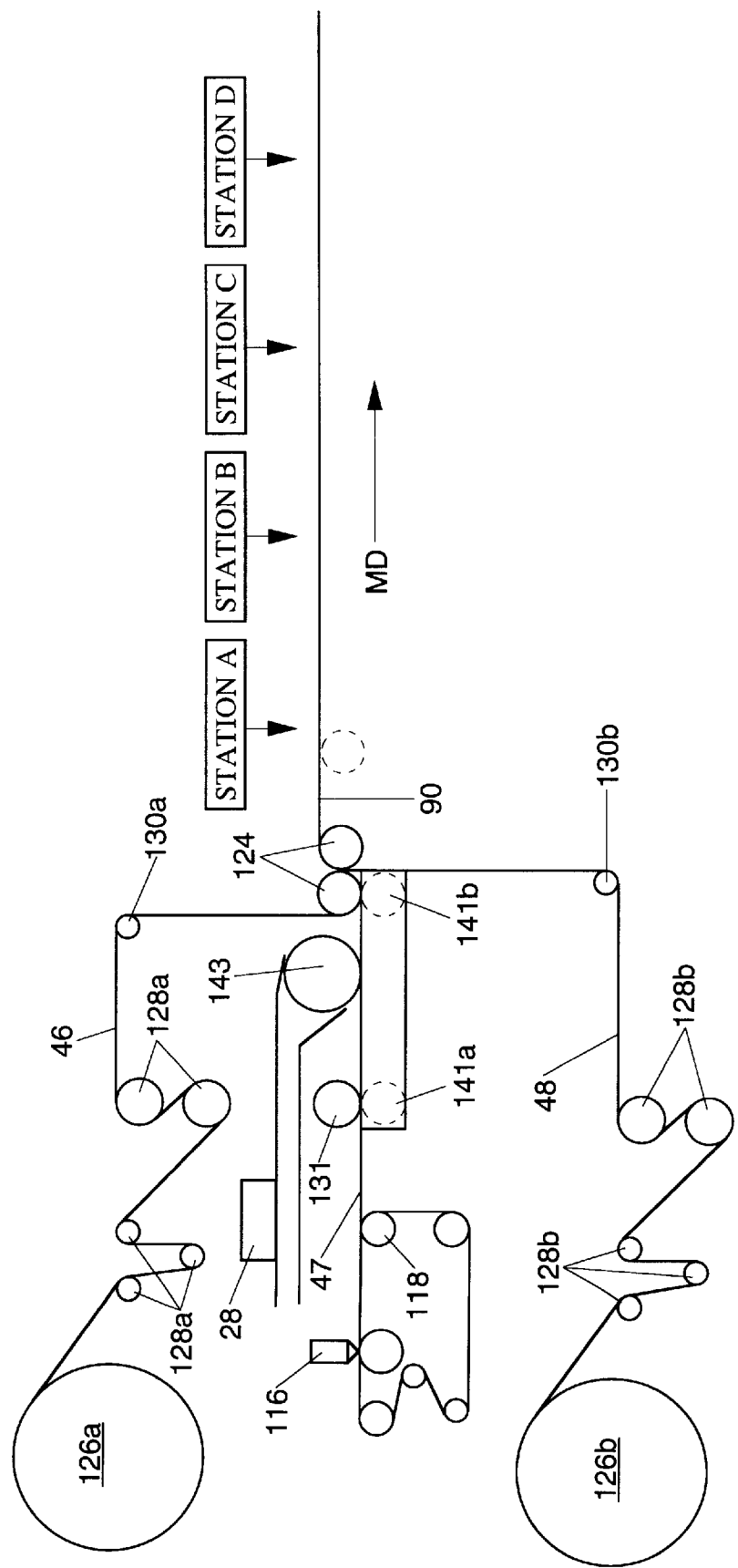
FIG. 8 is a side elevational schematic view of one apparatus which may be used to produce the disposable absorbent article of the present invention.
Figure 9:
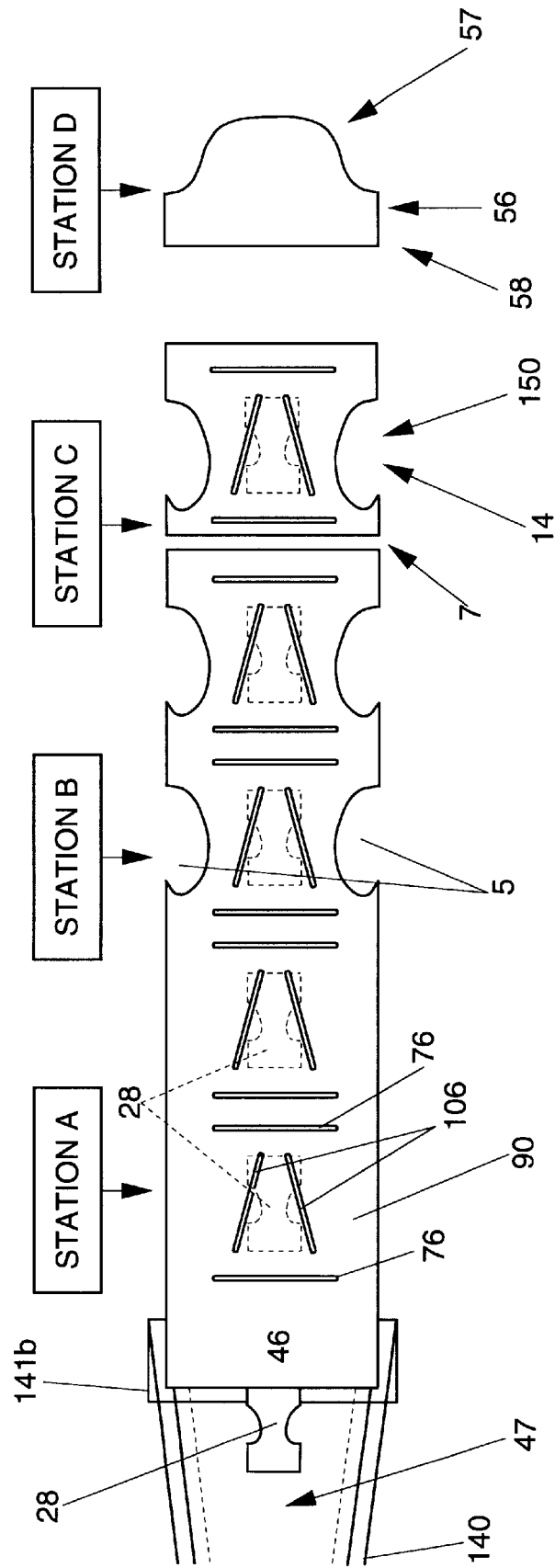
FIG. 9 is a top plan view of a portion of the apparatus shown in FIG. 8.

FIG. 8 is a schematic elevational view of an apparatus which may be used to form the disposable article of the present invention. FIG. 9 is a top plan view of a portion of the apparatus of FIG. 8 with line 112a, the application roll 131, and the combining rolls 124 deleted for clarity.

Referring to FIGS. 8 and 9, the absorbent core 28 is positioned on the elastomeric lamina 47 by the mat former 143, as the elastomeric lamina 47 is being stretched by the diverging belts 140. The elastomeric web 47 with the absorbent core 28 positioned thereon will then pass through the combining rolls 124 where the outboard laminae 46, 47 will be joined to the elastomeric lamina 47. Because the absorbent core 28 is positioned between the inner lamina 46 and the elastomeric lamina 47, the inner lamina 46 will function as a topsheet and therefore must be liquid pervious to allow liquids to be absorbed by the absorbent core 28.

Although in a preferred embodiment the absorbent assembly comprises an absorbent core 28 positioned between the inner lamina 46 and the elastomeric lamina 47, the absorbent assembly 22 may be applied to the chassis/laminate 90 after the laminate 90 is formed by the combining rolls 124, i.e., after the laminate 90 leaves the combining rolls 124. If the absorbent assembly 22 is to be an absorbent insert, as described hereinbefore, then it is preferred that the absorbent assembly 22 be applied to the laminate web 90 after the web 90 leaves the combining rolls 124.

Referring to FIGS. 8 and 9, the laminate 90 will be advanced from the combining rolls 124 to Station A at which various elements of the absorbent article will be applied, affixed, or secured to the laminate web 90, i.e., the chassis. Examples of the elements which may be applied to the laminate web 90 at Station A, include the absorbent assembly 22 (if it has not previously been applied to the elastomeric lamina 47), the inflected barrier leg cuffs 106, the gasketing leg cuff elastics 105, the elastic waistband members 76, the bloused outer cover 18, or the like. Generally, each element will be applied at a separate location or station on the manufacturing line. For clarity, however, the various stations will be shown in FIG. 8 as a single station (Station A). It should be understood that Station A may represent several different stations on the manufacturing line.

The laminate 90 web with the desired elements attached thereto, will then be conveyed from station A to a cutting station, Station B, where the leg notches 5 will be cut from the laminate web 90. The laminate 90 will then be conveyed to a severing station, Station C, where the web 90 will be severed into individual units 150 or chassis 14 having a front portion 56, a rear portion 58, and a crotch portion 57. The individual chassis 14 will be conveyed to a folding station, Station D, where each will be folded at about the crotch portion 57 such that the front portion 56 substantially superposes the rear portion 58.

The folded chassis 14 may then be seamed according to any of the methods or apparatus described hereinbefore. Alternatively, if an absorbent article resembling a baby diaper is preferred, securement tapes, as described hereinbefore, can be applied to the front portion 56 or the rear portion 58 of the chassis 14.

ALTERNATE EMBODIMENTS

Figure 5:
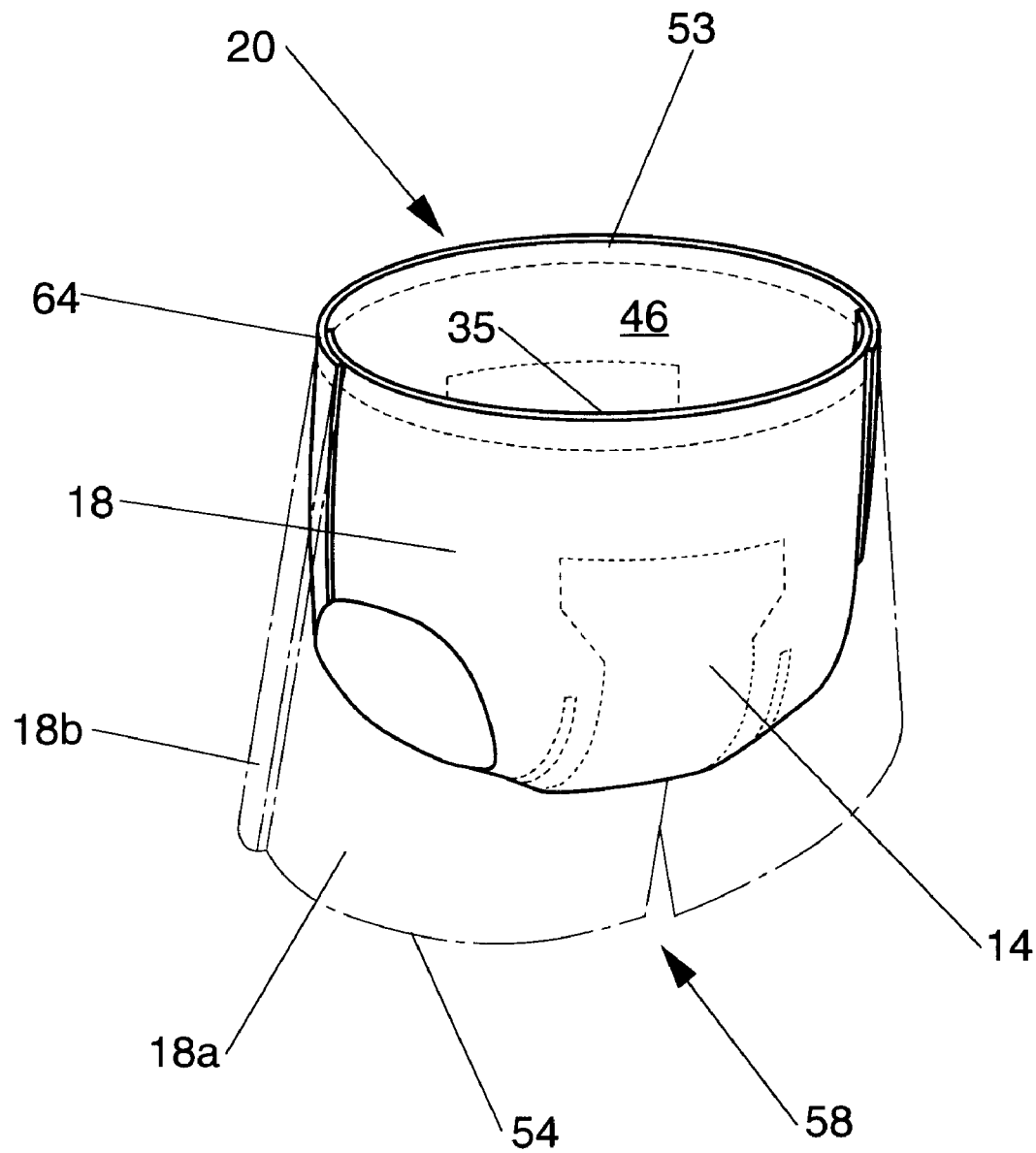
FIGS. 5 and 5A are perspective views of alternate embodiments of the present invention.
Figure 5A:
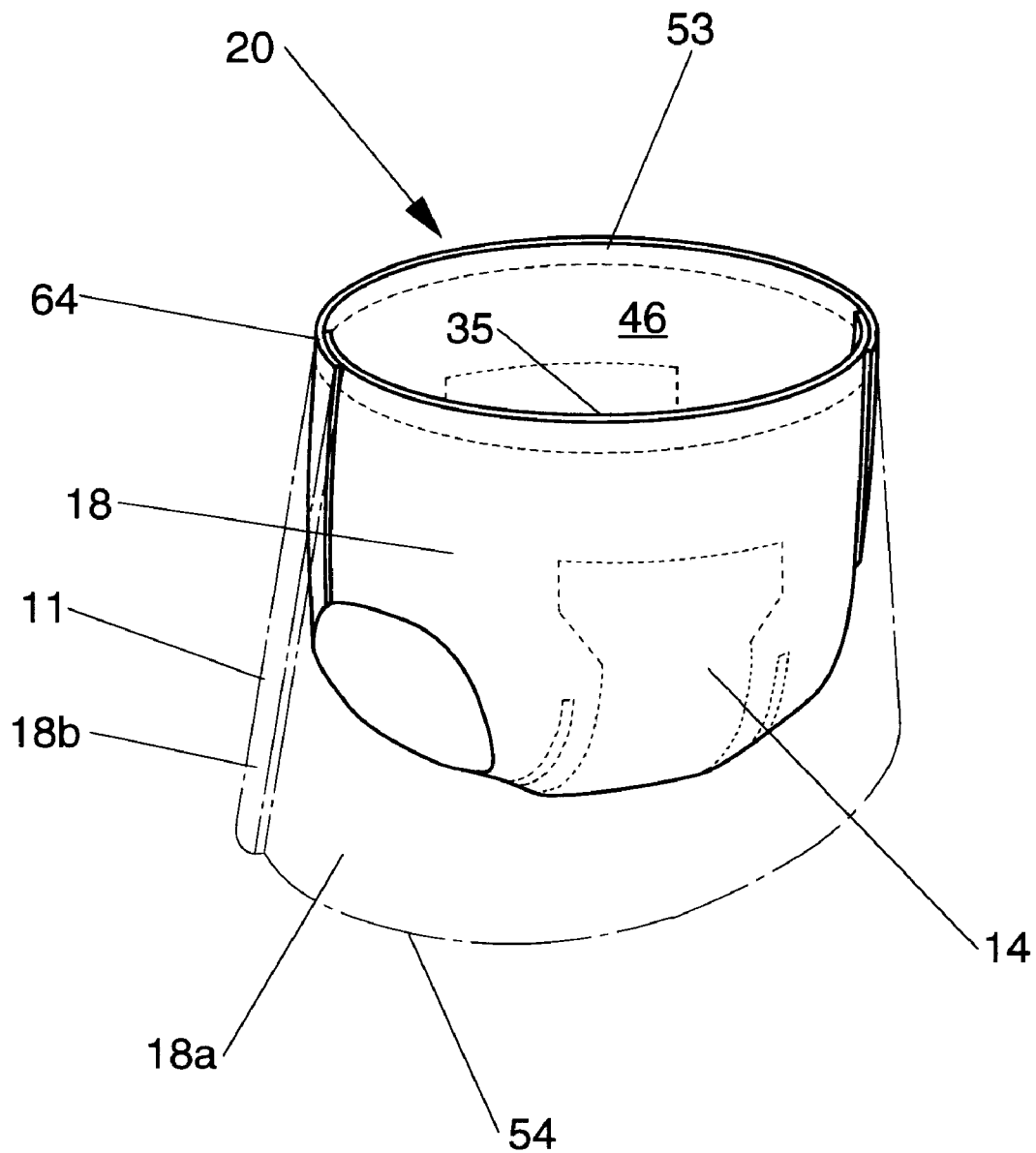

In alternative embodiments of the present invention, shown in FIGS. 5 and 5A, the outer cover 18 of the disposable garment 20 will comprise a first section 18a and a second section 18b, each having a top edge 53 which is secured to the chassis 14 and a bottom edge 54 which is not secured to the chassis 14. Preferably, the outer cover 18 will resemble a skirt or, alternatively, a pair of boxer-shorts, thereby substantially hiding the underlying chassis and providing a very garment-like appearance.

Referring to FIG. 5A, the top edge 53 of the first section 18a is joined to the waistband region 35 of the front portion 56 and the top edge 53 of the second section 18b is joined to the waistband region 35 of the rear portion 58. The waistband region 35 is that portion of the chassis 14 adjacent to the end edge 64 of the chassis 14. The top edge 53 of the first and second sections 18a, 18b may be joined to the waistband region 35 of the chassis 14 by any of the means well known in the art. Suitable methods of joining the top waist edge 53 of the outer cover 18 to the waistband region 35 of the chassis 14 would include adhesive bonding, ultrasonic bonding, heat sealing, or the like. Preferably, the first and second sections 18a, 18b of the outer cover 18 are extensions of other elements of the absorbent article, i.e., the topsheet, the backsheet, the inner lamina, the outer lamina, or the like. In a preferred embodiment, the first and second sections 18a, 18b of the outer cover 18 are extensions of the inner lamina 46 of the chassis 14. The side edges of the first section 18a are joined to the side edges of the second section 18b along seam 11. Suitable methods for joining the side edges of the first and second sections 18a, 18b, are described herein with respect to forming the side seams 10 of the absorbent article 20. It is also possible that the seam 11 joining the first section 18a to the second section 18b may be formed at the same time as the side seam 10 of the absorbent article 20. The bottom edges 54 of the first and second sections 18a, 18b extend below the crotch portion 57 of the chassis 14 in its typical in-use configuration such that the outer cover 18 encircles the elastomeric chassis 14 and substantially resembles a girl's skirt.

In another alternate embodiment, shown in FIG. 5, the absorbent article 20 comprises an outer cover 18 and is substantially the same as the absorbent article shown in FIG. 5A and described above. However, the absorbent article of FIG. 5 has an outer cover 18 that is notched such that it resembles a pair of boxer-shorts. Referring to FIG. 5, the bottom edge 54 of the front section is joined to the bottom edge 54 of the second section 18b at central notch 58. The central notch 58 may be formed by any of the means well known in the art. For example, the notch may be formed by bonding (e.g., adhesively bonding, ultrasonically bonding, heat sealing, or the like) a portion of the first section 18a to a portion of the second section 18b and then cutting the notch into the bonded area. Preferably, the notch 58 is formed by simultaneously cutting and bonding the first section 18a and the second section 18b, e.g., ultrasonically cutting and bonding, thermally cutting and bonding, or the like. Although the notch 58 is shown as resembling an upside-down V-notch, it should be understood that the notch may be of various shapes. For example, the notch may resemble an upside-down U-shape, may be a slit, or the like.

While particular embodiments of the present invention have been illustrated and described, it would be obvious to those skilled in the art that various other charges and modifications can be made without departing from the spirit and scope of the invention. It is therefore intended to cover in the appended claims all such changes and modifications that are within the scope of this invention.

What is claimed is:

1. An elasticized disposable training pant comprising:
   an elastically extensible chassis having a front, portion having a waistband, a rear portion having a waistband, a crotch portion, end edges, longitudinal side edges, a periphery adjacent to said end edges and said longitudinal side edges, and a central region inboard of said periphery, said chassis comprising an elastomeric laminate comprising:

an elastomeric, pressure-sensitive adhesive film, a first laterally gathered lamina joined to a first side of said adhesive film, and a second laterally gathered lamina joined to a second side of said adhesive film;

an absorbent core positioned between said adhesive film and said first lamina; and fixed side seams joining said front portion to said rear portion to form two leg openings and a waist opening substantially encircled by said end edges.

2. The training pant of claim 1 additionally comprising a nonwoven outer cover having a periphery and a central region inboard of said periphery, at least a portion of said periphery of said outer cover being joined to at least a portion of said periphery of said chassis such that said central region of said outer cover is at least partially detached from said central region of said chassis such that said outer cover is bloused from said chassis.

3. The training pant of claim 2 wherein said outer cover has a front top edge, a rear top edge, a front bottom edge, and a rear bottom edge, said front top edge being joined to said waistband of said front portion and said rear top edge being joined to said waistband of said rear portion, and said front bottom edge and said rear bottom edge extend below said crotch portion of said chassis.

4. The training pant of claim 3 wherein a portion of said first bottom edge is secured to a portion of said rear bottom edge by a notch positioned at about said crotch portion of said chassis such that said outer cover resembles a pair of boxer shorts.

* * * * *

UNITED STATES PATENT AND TRADEMARK OFFICE
CERTIFICATE OF CORRECTION

PATENT NO. : 6,149,637
DATED : November 21, 2000
INVENTOR(S) : Allen et al.

It is certified that error appears in the above-identified patent and that said Letters Patent is hereby corrected as shown below:

Column 3,
Line 23, please delete "to the direction transverse".
Lines 24 and 26, please delete "1" and insert therefor -- *l* --.

Column 4,
Line 23, after "Wis.", please delete "in".

Column 5,
Lines 52 and 57, please delete "1" and insert therefor -- *l* --.
Line 65, after "t", please delete "1".

Column 9,
Line 19, please delete "1" and insert therefor -- *l* --.

Column 10,
Line 50, please delete "ah" and insert therefor -- an --.

Column 13,
Line 9, please delete "method" and insert therefor -- methods --.

Column 16,
Line 66, after "front" please delete "," (the comma).

Signed and Sealed this

Fifth Day of July, 2005

JON W. DUDAS
*Director of the United States Patent and Trademark Office*